(12) United States Patent
Li

(10) Patent No.: US 8,337,889 B2
(45) Date of Patent: Dec. 25, 2012

(54) SMECTITE DISPERSIBLE TABLETS AND THE PREPARATION THEREOF

(75) Inventor: Shibiao Li, Shandong (CN)

(73) Assignee: Shandong Luye Pharmaceutical Co., Ltd., Shandong (CN)

( * ) Notice: Subject to any disclaimer, the term of this patent is extended or adjusted under 35 U.S.C. 154(b) by 1432 days.

(21) Appl. No.: 11/597,219

(22) PCT Filed: May 23, 2005

(86) PCT No.: PCT/CN2005/000715
§ 371 (c)(1),
(2), (4) Date: Oct. 23, 2007

(87) PCT Pub. No.: WO2005/112881
PCT Pub. Date: Dec. 1, 2005

(65) Prior Publication Data
US 2008/0038337 A1 Feb. 14, 2008

(30) Foreign Application Priority Data
May 21, 2004 (CN) .......................... 2004 1 0042539

(51) Int. Cl.
*A61K 9/46* (2006.01)
*A61K 9/20* (2006.01)
(52) U.S. Cl. .................... 424/466; 424/464; 424/465
(58) Field of Classification Search .................... None
See application file for complete search history.

(56) References Cited

U.S. PATENT DOCUMENTS 5,556,639 A * 9/1996 Fielden .................... 424/480
6,399,591 B1 * 6/2002 Lee et al. .................... 514/63
2002/0115583 A1 * 8/2002 Lant et al. .................... 510/445
2003/0095906 A1 * 5/2003 Bauer et al. .................... 423/333
2009/0186081 A1 * 7/2009 Holm et al. .................... 424/464

FOREIGN PATENT DOCUMENTS

WO WO 01/09278 2/2001

OTHER PUBLICATIONS

PCT/ISA/220, "Notification of Transmittal of the International Search Report and the Written Opinion of the International Searching Authority, or the Declaration" for PCT/CN2005/000715, (3 pgs.).
PCT/IPEA/409, "International Preliminary Report on Patentability" for PCT/CN2005/000715, (5 pgs.) (with translation, 5 pgs.).
PCT/ISA/210, "International Search Report" PCT/CN2005/000715, (6 pgs.) (with translation, 4 pgs.).
Communication from the EPO for European Patent Application No. 05 752 400.1-2123, mailed May 17, 2011 (3 pgs.).

* cited by examiner

*Primary Examiner* — Susan Tran
(74) *Attorney, Agent, or Firm* — John C. Pokotylo; Straub & Pokotylo

(57) ABSTRACT

A smectite dispersible tablet and the preparation progress thereof are disclosed, which is a new pharmaceutical formulation of smectite comprising smectite, a filler and a disintegrant. The dispersible tablet is stable in quality, can disintegrate quickly and disperse homogeneously, which is easy in dosage control, convenient in transportation and packaging, and has a flavor taste, a smooth surface as well as a uniform color.

2 Claims, No Drawings

SMECTITE DISPERSIBLE TABLETS AND THE PREPARATION THEREOF

TECHNICAL FIELD

The invention relates to a new pharmaceutical preparation of smectite, specifically, to the smectite dispersible tablets and a process for preparing the same.

BACKGROUND ART

Being a common epidemic disease, diarrhea gravely jeopardizes human health. According the survey of the World Health Organization (WHO), diarrhea has the fourth highest lethality among various diseases, just following tumors, cardio/cerebral-vascular diseases and diabetes. The most direct complications of diarrhea are dehydration, electrolyte disturbance, and malabsorption. Rehydration and adequately sustaining on diet are recommended during the therapy, but rehydration per se cannot treat the origin of diarrhea, nor could significantly shorten the duration or number or amount of diarrhea, thus appropriate drug treatment is of necessity. WHO has proposed six criteria for diarrhea drugs as follows: (1) highly effective; (2) orally administrable; (3) combinable with oral rehydration solutions (ORS); (4) intestinally unabsorbable; (5) not affecting intestinal absorption, especially the absorption of glucose and amino acids; (6) resistant to a series of intestinal pathogens.

Smectite is the main component of bentonite, and is conventionally used as absorbents, etc. In recent years, it has been found that smectite can be used as a highly effective digestive tract mucoprotectant and an absorbent for viruses, bacteria and toxins thereof, and can be used for the treatment of various acute or chronic diarrheas.

In the researches, the results indicate that smectite have pathogen clearance and mucoprotective actions in digestive tract, and is a safe and highly effective anti-diarrhea drug and meets the criteria of WHO as above mentioned. In addition, smectite not only can clear pathogens and toxins thereof, but also exhibits digestive muco-barrier protecting, enhancing and repairing functions, and can improve the quality of mucous fluid, balance the normal flora, and promote regeneration and reparation of the epithelial cells.

Pharmacological tests and clinical-study results show that the pharmacological effects of smectite depend on its unique laminate structure, inhomogeneous electric distribution and glid-viscoplasticity, so that smectite can continuously and uniformly cover the digestive tract surface and exhibit therapeutic effects via electrostatic and physicochemical properties. Smectite has good therapeutic effects on various acute and chronic diarrheas, reflux esophagitis, chronic gastritis, peptic ulcer, irritable bowel syndrome, and inflammatory bowel diseases. Further, smectite exhibits significant therapeutic effects on some clinical stubborn diseases, such as stress ulcer, stomatitis and digestive complications caused by large dosed radio- or chemo-therapy. Thus, smectite expands clinical therapeutic means and is an ideal digestive muco-protectant at present.

Smectite has a high safety, is easily to be accepted by patients and is especially suitable for those patients who should be specifically cared in medications, such as infants, pregnant women, aged people and patients with hepato/renal dysfunction.

However, currently commercially available pharmaceutical dosage form of smectite is powder (dioctahedral smectite powder), but this dosage form still has some drawbacks, such, it is not convenient to take the powder; the dose can hardly be precisely controlled; and it should be homogenous stirred before oral administration of the power. The powder has sand sensation and bilgy odour, so that patients often feel unpleasant while taking the powder. On the other hand, the powder can hardly be precisely divided when it is administrated to infants and children by a reduced dose.

DISCLOSURE OF THE INVENTION

The invention provides a novel smectite dispersible tablet and a process for preparing it.

The smectite dispersible tablet of the invention comprises smectite, a filler and a disintegrant.

The smectite dispersible tablet of the invention preferably comprises 3-20 parts-by-weight of filler and 1-8 parts-by-weight of disintegrant based on per 100 parts-by-weight of smectite; most preferably comprises 10 parts-by-weight of filler and 3 parts-by-weight of disintegrant based on per 100 parts-by-weight of smectite.

Wherein, said disintegrant is preferably sodium starch glycolate, low-substituted hydroxypropyl cellulose, croscarmellose sodium, or a combination of two or more of the above.

Said filler is preferably microcrystalline cellulose, carboxymethyl starch, starch, or a combination of two or more of the above.

The smectite dispersible tablet of the invention may further comprise a correctant.

Each smectite dispersible tablet of the invention can absorb 0.3-0.5 g of strychnine sulfate.

The process for preparing the said smectite dispersible tablet is characterized by comprising: uniformly mix the filler and smectite by the isochoric incremental method, preferably, add the disintegrant simultaneously, and if necessary, add the correctant before, simultaneously or after mixing; granulate; followed by subsequently add the disintegrant, mix uniformly and compress the tablets; alternatively, the granule so obtained may be tableted directly; optionally, other tablet excipients may be added during tableting.

BEST MODE FOR CARRYING OUT THE INVENTION

The substantial components of the smectite dispersible tablet of the invention are smectite, filler and disintegrant.

In the invention, smectite may be any pharmaceutically acceptable smectite, preferably those satisfy the pharmaceutical standards in a country.

The filler is any water-soluble or water-insoluble filler. The water-soluble filler may be such as lactose, sucrose, mannitol, sorbitol, methyl cellulose, hydroxypropyl cellulose, hydroxypropyl methyl cellulose, and dextrin, etc.; and the water-insoluble filler may be such as microcrystalline cellulose, calcium carbonate, calcium sulfate, calcium hydrogen phosphate, starches (potato starch, corn starch, and wheat starch, etc.), and carboxymethyl starches, etc. Preferably, the filler of present invention is a water-insoluble filler, more preferably one or two or more of microcrystalline cellulose and starches.

Smectite per se is a powder and can hardly be molded, therefore the commercially available smectite preparations are all powders up to now. However, the inventors of the invention have surprisingly found that smectite could be tableted upon addition of a suitable filler to improve the compress-molding property thereof. And the invention is finished thereby.

In case that the amount of filler added into smectite is too little, the compress-molding property of smectite may not be improved sufficiently; on the other hand, if an excessive amount of filler is added, the disintegrability or dissolubility of the dispersible tablets of present invention may decrease, or the smectite may not function properly; in both cases, the object of the invention may not be achieved. Thus, although the amount may differ depending on the filler used, it is preferably to have at least 1 part by weight or more, preferably 3 parts by weight of filler with respect to 100 parts by weight of smectite. The upper limit of filler is not specially restricted so far as the disintegrability and dissolubility of smectite are not affected, but preferably is not more than 50 parts by weight, more preferably 20 parts by weight or less.

The disintegrant of the invention may be any pharmaceutically acceptable conventional disintegrant or swelling excipients. The disintegrant may be such as dry starch, sodium starch glycolate, microcrystalline cellulose, low-substituted hydroxypropyl cellulose, crospovidone, croscarmellose sodium, microcrystalline cellulose, natural clay silica alumina-magnesia, etc.; and the swelling excipients may be such as guar gum, cocklebur gum, alginate, dextran, pressable starch, pregelled starch, polysaccharides, and hydrophilic polymers, such as calcium carboxymethyl cellulose, hydroxyl-propyl methyl cellulose, hydroxypropyl cellulose, etc.

It has been found by the present inventors that the smectite dispersible tablet of the invention can disintegrate and dissolve rapidly with suitable disintegrants.

Preferably, the disintegrant in the invention is any one of sodium starch glycolate, low-substituted hydroxypropyl cellulose, croscarmellose sodium, or a combination of two or more of the above.

In case that the amount of disintegrant in the smectite dispersible tablet of the invention is not enough, the disintegrability and dissolubility might not be sufficient; on the other hand, if an excessive amount of disintegrant is added, the disintegrability will not be further improved, but the cost increases. Thus, the amount of disintegrant is at least 0.5 parts by weight or more, preferably at least 1 part by weight, with respect to 100 parts by weight of smectite. The upper limit of the amount of disintegrant may be determined according to the desired disintegrating speed and is not specifically limited, however, from the view of cost optimization, the amount is preferably not excessing 20 parts by weight, as more than 20 parts of weight of disintergrant will not further improve the disintegrating speed. More preferably, the disintegrant is in an amount of 8 parts by weight or less.

The disintegrant in the smectite dispersible tablet of present invention may be added into the granules prior tableting (exo-disintegrant) or be added into the mixture for granulating (inner-disintegrant).

For better disintegrability, it is preferred that both exo- and inner-disintegrants are used. In this case, the amount of inner-disintegrant is preferably being 20-50% by weight with respect to the total weight of disintegrants.

More preferably, 10 parts by weight of the filler and 3 parts by weight of the disintegrant are comprised per 100 parts by weight of smectite, and the ratio of the disintegrants is 1 part by weight of inner-disintegrant vs. 2 parts by weight of exo-disintegrant.

For a better taste of the dispersible tablets of the invention, a suitable amount of correctant and/or fragrance (generalized as "correctant") may be comprised. The correctant may be any correctant commonly used in the field, preferably any one selected from stevioside, saccharin sodium, aspartame, vanillin, and ethyl vanillin, or a combination of two or more of the above. And the amount and type of the correctant are not limited in the invention.

If desired, other pharmaceutically acceptable excipients, such as suitable amount of glidant, antisticking agent and lubricant (generalized as lubricant), etc., such as micropowder silica gel, magnesium stearate, talc powder, polyethylene glycol, hydrogenated vegetable oil, polyethylene glycol, magnesium (sodium) dodecyl sulfate, etc., can also be used in the invention. Upon selection, the affect thereof on the hardness, disintegrability or dissolubility of the dispersible tablet should be considered. The use of these other adjuvants is not restricted so far as they do not affect the disintegrability of tablets in the invention.

The smectite dispersible tablet of the invention can be prepared via conventional method in the field, for example, by conventional granulation-press method or direct press method.

In the granulating-press method, the granules may be formed via wet granulation process or dry granulation process. The wet granulation process comprises the steps of mixing smectite and filler, and adding the correctant and/or the disintegrant if desired; adding a solvent to form a soft material, wherein the solvent may be water and/or ethanol; granulating the soft material, drying and sieving, and then adding a lubricant, and optionally adding a disintegrant simultaneously; and mixing and tableting to give the tablets. The dry granulation process comprised the steps of mixing smectite and the filler, and adding the correctant and/or the disintegrant if desired; compressing the mixture to form blocks, pulverizing and sieving; then adding a lubricant, and adding the disintegrant simutanously if desired; and mixing and tableting to give the tablets.

The direct press process comprises the steps of mixing smectite with the filler and the disintegrant, adding the correctant and/or the lubricant if desired, uniformly mixing, and tableting.

The preferred preparation process comprises the steps of mixing homogeneously smectite and the filler by the isochoric incremental method, preferably adding the disintegrant simultaneously, if necessary, adding the correctant before, simultaneously or after mixing, granulating, followed by adding the disintegrant, mixing homogenuously and tableting, alternatively, the granules so obtained may directly pressed after addition of a lubricant, to prepare the dispersible tablets of the invention.

As described above, the disintegrant may be added internally (inner-disintegrant) or externally (exo-integrant) or internally and externally, preferably adding both inner and exo-integrants, wherein the inner-disintegrant and the exo-disintegrant may be same or different, independently selected from the aforementioned disintegrants.

Preferably, as described above, the inner- and exo-disintegrant in the invention may be any one selected from sodium starch glycolate, low-substituted hydroxypropyl cellulose, croscarmellose sodium, or a combination of two or more of the above.

The weight ratio of the inner- and exo-disintegrant is 1:1-4, preferably 1:2.

The smectite dispersible tablets of the invention having the above compositions and being prepared from the above described processes can maintain the absorption properties of smectite, while improve the drawbacks of bad taste in the conventional smectite powders, in addition, can be easily administered to the infants in a reduced amount.

The properties of the smectite dispersible tablet of the invention will be described as follows.

On average, the smectite dispersible tablet of the invention can absorb 0.3-0.5 g of strychnine sulfate $(C_{42}H_{44}NO_4 \cdot H_2SO_4 \cdot 5H_2O)$ per gram of the tablet. If the absorption quantity is less than 0.3 g, the smectite's absorption property is not sufficient, on the other hand, if the absorption quantity is more than 0.5 g, extra cost is needed for special processes, both cases are not preferred.

The absorption capacity is measured according to the following method.

Provide 10 tablets, pulverize finely. Then place a suitable amount of the powder (equivalent to about 0.2 g of smectite), accurately weighed, in a conical flask with a plug. Add accurately 10 ml of phosphate buffer solution (pH 6.8). After shaking for 1 hour, the conical flask is stood for 24 hours. Add accurately 10 ml of strychnine sulfate solution (which is obtained by the following steps: place about 2 g of strychnine sulfate, accurately weighed, in a 100 ml volumetric flask, add a suitable volume of water, heat in water-bath to dissolve, cool to room temperature, add water to volume and agitate), and the conical flask is shaked for 1 hour in a 37° C. water-bath and filtered. Transfer accurately 10 ml of the filtrate to a 250 ml volumetric flask, dilute to volume with phosphate buffer solution (pH 6.8) and shake. Transfer accurately 5 ml of the solution to a 50 ml volumetric flask, dilute to volume with phosphate buffer solution (pH 6.8) and agitate, determine the absorbance at 254 nm according to spectrophotometry (c.f. Part II, Annex IV, Section 1 of Pharmacopoeia of the People's Republic of China 2000). Concomitantly, a 20 μg per mL of strychnine sulfate phosphate buffer solution (pH 6.8) (control solution) is prepared from the same strychnine sulfate solution and the absorbance thereof is determined in the same method. The absorption capacity is calculated according to the following formula.

$$\text{Absorption capacity } (g) = \frac{(2A_1 - A_2) \times M_1 \times D_2 \times M_3}{M_2 \times A_1 \times D_1 \times G}$$

$A_1$: the absorbance of strychnine sulfate control solution
$A_2$: the absorbance of the sample solution
$M_1$: the weight of strychnine sulfate
$M_2$: the weight of sample
$M_3$: the average weight of a tablet
$D_1$: the dilution folds of the strychnine sulfate control solution
$D_2$: the dilution folds of the sample solution
G: the specification quantity The above absorption capacity is equivalent to that of the commercially available smectite powders (dioctahedral smectite powders).

The smectite dispersible tablets of the invention contain about 60-98%, preferably about 80.0-95.0% of smectite.

The smectite content is determined according to the following method:

Provide 10 tablets, pulverize finely. Then place a suitable amount of the powder (equivalent to about 0.2 g of smectite), accurately weighed, in a crucible which has a constant weight, then the crucible is ignited at 1000±50° C. to another constant weight, and the smectite content can be determined by calculation.

The dispersible tablet of the invention having the above compositions and being prepared according to the above process has excellent disintegrability and can completely disintegrate within 1 minute.

The disintegration is determined according to the following method.

Observing the disappearing time of the dispersible tablets with a up-and-down type disintegration tester with a hoistable metal bracket and a basket having a sieve at the lower end, which moves up and down in the water of 37±1° C. at a frequency of 30-32 cycles per minute.

The dissolution rate of the smectite dispersible tablets of the invention (the amount of smectite that can disperse homogenously in water) should be 70% or more of the tablet weight. The smectite dispersible tablet of the invention can rapidly disperse in water when its dissolubility is 70% or more, and thus the therapeutic effect of the dispersible tablet can be ensured.

The dissolution rate is determined according to the following method.

The dissolution rate of dispersible tablets is determined following the protocol of the blade method for measuring the dissolution rate, e.g. measuring in solvent, 900 ml of water; rotation speed, 200 rpm, after 45 minutes, place 100 ml of solution in an evaporating dish which has been dried at 105° C. to constant weight. Evaporate to dry on a water-bath, further dry the evaporating dish at 105° C. for another 3 hours, and then weigh and calculate. The dissolution rate should be 70% or more, comparing with the actual tablet weight.

In the invention, since smectite is not actually absorbed in the intestinal tract, the dosage amount of the smectite dispersible tablet is not limited, as far as the human body can accept. However, if too much smectite is administered, constipation or ex-dried feces, etc. will occur due to the adsorption effect of smectite. Thus, excessive administration should be avoided, and the administration dosage for adults, infants/young children or aged people may be ordinarily 0.5-15 g daily, although this may vary depending on the age, body weight and seriousness of the disease.

According to the range of administration, the smectite dispersible tablets of the invention may be prepared in different dosages, such as 0.5 g per tablet, 1 g per tablet, 2 g per tablet, etc., so that a reasonable assignment dosage can be achieved by using integer folds of the minimum dosage unit.

The smectite dispersible tablet of the invention is preferably a dispersible tablet having a dosage of 1 g per tablet.

The smectite dispersible tablets of the invention are gray or whiteous with fragrant and sweet taste. For adults, the administration dosage may be 3 tablets (1 g per tablet) once and three times daily. For infants or young children, it could be 1 tablet (0.5 g per tablet or 1 g per tablet) once and 2-3 times daily, and such dosage may be increased to 2 tablets once with the increase of age.

EXAMPLES

The invention is further illustrated by the following examples and test examples, but the invention is not limited to the examples.

The smectite used hereinafter is identified as follows:

(1) Place smectite fine powder and calcium fluoride, 0.5 g respectively, in a platinum crucible. Add 1 ml of concentrated sulfuric acid to moisten, cover the crucible by a transparent plastic plate having a drop of water thereon. If necessary, heat slightly. A white colloid is formed on the surface of water drop;

(2) Place 1.0 g of smectite fine powder in a ceramic evaporating dish. Add 10 ml of water and 5 ml sulfuric acid. Heat to generate a white smoke, cool and add 20 ml of water slowly, boil 2-3 minutes, filter. The filtrate is aluminum salt identification test positives, for example, a while colloid precipitation is formed upon addition of sodium hydroxide solution to the filtrate, which dissolves in an excessive sodium hydroxide solution; or a while colloid precipitation is formed upon addition of aqueous ammonia to the filtrate, which exhibits cherry-red color when sodium alizarinsulfonate indicator is added (see also the Part II, Annex III of the Pharmacopoeia of the People's Republic of China 2000).

Tested Items:

Particle fineness: Add 50 ml of water to 10 g of the powder sample, shake to disperse. The mixture is vigorously stirred for 15 minutes (rotation speed not lower than 5000 rpm); the stirred mixture is poured onto a 45 μm sieve that has been moistened with water, then the sieve is rinsed with water until clear. The residue on the sieve is transferred into a crucible (dried to a constant weight) with wash bottle, and the crucible is slowly heated to 500-600° C. and kept for 2 hours, and the residue shall be no more than 0.1 g.

Silica: 10 g of sample is provided and finely milled. Place a suitable amount of powder equivalent to about 0.5 g of smectite, accurately weighed, in a platinum crucible. Add sodium carbonate and potassium carbonate, 0.5 g each, mix. Ignite at 800° C. for 3 hours after slowly elevation of temperature, and then cool. Add a total amount of 50 ml diluted hydrochloric acid in portions. Dissolve the residue completely under stirring and transfer the solution into a 250 ml beaker. The crucible is washed with a small amount of water for several times, the water for washing is combined into the beaker. Evaporate about one-half volume of the solution over heating, and then cool the beaker. Add 20 ml of hydrochloric acid and 1 ml of 2% gelatin solution, incubate at 60-70° C. on a water bath for 10 minutes, stir the solution from time to time, and filter the solution when it is hot. Wash the containers with hot water, collect the filtrate and washing water; and filter paper and residue are transferred to a crucible that has been burned to constant weight, then the crucible is ignited at 1100° C. to another constant weight, and the silica content is calculated and shall be no less than 500 mg per gram of sample.

Alumina ($Al_2O_3$): place the above collected filtrate and washing water in a 250 ml volumetric flask, dilute to volume with water and mix. Measure accurately 75 ml of the resultant solution, neutralize with aqueous ammonia test solution to just generate a white precipitation, then add diluted hydrochloric acid dropwisely to just dissolve the white precipitation, filter. Add 10 ml of acetic acid-ammonium acetate buffer solution (pH 6.0) and then about 25 ml of disodium ethylenediamine tetraacetate volumetric solution (0.05 mol/L), boil the filtrate solution for 5 minutes and cool to room temperature. Add 1 ml of xylenol orange indicator solution, titrate the solution with zinc volumetric solution (0.05 mol/L) to just becoming red, then add 0.4 g of sodium fluoride, boiling for 2 minutes, and cool. Titrate with zinc volumetric solution (0.05 mol/L) until the solution changes from yellow to red. Per ml of zinc volumetric solution (0.05 mol/L) is equivalent to 2.549 mg of $Al_2O_3$. The content of alumina shall be no less than 100 mg per gram.

Example 1

Smectite: 1000 g; microcrystalline cellulose: 100 g; sodium starch glycolate: 30 g; saccharin sodium: 2.34 g; vanillin: 1.34 g; aspartame: 1.0 g.

Preparation process: mixing saccharin sodium, aspartame and vanillin homogenously, then mixing with microcrystalline cellulose, smectite and 10 g of sodium starch glycolate with isochoric incremental method, granulating, drying and sieving. Adding 20 g of sodium starch glycolate, mixing homogeneously, and tableting. 1000 tablets were obtained.

Example 2

Smectite: 1000 g; microcrystalline cellulose: 200 g; sodium starch glycolate: 21 g; aspartame: 5.0 g.

Preparation process: mixing aspartame with microcrystalline cellulose, smectite and 7 g of sodium starch glycolate with isochoric incremental method, granulating, drying and sieving, adding 14 g of sodium starch glycolate, mixing homogenously, and tableting. 1000 tablets were obtained.

Example 3

Smectite: 1000 g; microcrystalline cellulose: 50 g; sodium starch glycolate: 50 g; saccharin sodium: 2.34 g; aspartame: 1.0 g.

Preparation process: mixing saccharin sodium and aspartame homogenously, then mixing with microcrystalline cellulose, smectite and 10 g of sodium starch glycolate with isochoric incremental method, granulating, drying, and sieving, adding 40 g of sodium starch glycolate, mixing homogeneously, and tableting. 1000 tablets were obtained.

Example 4

Smectite: 1000 g, carboxymethyl starch: 100 g; sodium starch glycolate: 10 g; low-substituted hydroxypropyl cellulose: 20 g; vanillin: 1.34 g; aspartame: 3.0 g.

Preparation process: mixing aspartame and vanillin homogenously, then mixing with microcrystalline cellulose, smectite and 10 g of sodium starch glycolate with isochoric incremental method, granulating, drying and sieving, adding 20 g of low-substituted hydroxypropyl cellulose, mixing homogeneously, and tableting. 1000 tablets were obtained.

Example 5

Smectite: 1000 g; microcrystalline cellulose: 100 g; sodium starch glycolate: 30 g; sodium saccharin: 2.34 g; vanillin: 1.34 g; aspartame: 1.0 g.

Preparation process: mixing saccharin sodium, aspartame and vanillin homogenously, then mixing with microcrystalline cellulose, smectite and 30 g of sodium starch glycolate with isochoric incremental method, granulating, drying and sieving, and tableting. 1000 tablets were obtained.

Example 6

Smectite: 1000 g; microcrystalline cellulose: 100 g; croscarmellose sodium: 30 g; saccharin sodium: 2 g; vanillin: 1 g; aspartame: 1.0 g.

Preparation process: mixing saccharin sodium, aspartame and vanillin homogenously, then mixing with microcrystalline cellulose, smectite and 10 g of croscarmellose sodium with isochoric incremental method, granulating, drying and sieving, adding 20 g of croscarmellose sodium, mixing homogeneously, and tableting. 1000 tablets were obtained.

Example 7

Smectite: 1000 g; microcrystalline cellulose: 100 g; croscarmellose sodium: 30 g; sodium saccharin: 2.34 g; vanillin: 1.34 g; aspartame: 1.0 g.

Preparation process: mixing saccharin sodium, aspartame and vanillin homogenously, then mixing with microcrystalline cellulose, smectite and 10 g of croscarmellose sodium with isochoric incremental method, granulating, drying and sieving, adding 20 g of croscarmellose sodium, mixing homogeneously, and tableting. 2000 tablets were obtained.

Example 8

Smectite: 1000 g; microcrystalline cellulose: 100 g; sodium starch glycolate: 30 g; sodium saccharin: 2.34 g; vanillin: 1.34 g; aspartame: 1.0 g.

Preparation process: mixing saccharin sodium, aspartame and vanillin homogenously, then mixing with microcrystalline cellulose, smectite and sodium starch glycolate with isochoric incremental method, granulating, drying and sieving, and tableting. 1000 tablets were obtained.

Example 9

Smectite: 1000 g; microcrystalline cellulose: 100 g; sodium starch glycolate: 30 g; aspartame: 4.0 g.

Preparation process: mixing aspartame with microcrystalline cellulose and smectite with isochoric incremental method, then adding sodium starch glycolate and mixing homogeneously, granulating, drying and sieving, and tableting. 1000 tablets were obtained.

Test Examples

The dispersing homogeneity of the smectite dispersible tablets of the invention was evaluated.

Samples: the smectite dispersible tablets obtained in Examples 1-9

Test method: Place two tablets of the smectite dispersible tablets of each Example in 100 ml of 20±1° C. water, shake, and pass through No. 2 sieves.

Test results: the disintegrating time of smectite dispersible tablets of each Example was within the range of 45 to 55 seconds, and all samples passed through the No. 2 sieve (internal aperture diameter 850±29 μm).

INDUSTRIAL APPLICABILITY

The smectite dispersible tablets of the invention can be used for the treatment of acute and chronic acute and chronic diarrhea, gastritis, esophagitis, colonitis, gastroesophageal reflux, irritable bowel syndrome, alteration of intestinal flora in adults and children. The smectite dispersible tablets of the invention can further be used for the adjunctive therapy of pains caused by gastric, esophagus and dodecadactylon diseases.

Furthermore, the smectite dispersible tablets of the invention exhibits good therapeutic effects, facilitates the control of dosage, the transportation and carrying, has better taste for oral administration and merits of smooth surface and uniform color.

What is claimed is:

1. An oral smectite dispersible tablet consisting essentially of:
   a smectite;
   3-20 parts by weight of a filler; and
   1-8 parts by weight of a disintegrant with respect to 100 parts by weight of the smectite, wherein said disintegrant is sodium starch glycolate, low-substituted hydroxypropl cellulose, croscarmellose sodium, or a combination thereof, and wherein said filler is microcrystalline cellulose, carboxymethyl starch, starch, or a combination thereof, wherein the amount of smectite in the tablet is about 60-98%.

2. The oral smectite dispersible tablet according to claim 1 having an absorption property characterized by its ability to absorb 0.3-0.5g of strychnine sulfate per gram of tablet.

* * * * *